United States Patent
Schwarz et al.

(10) Patent No.: US 12,116,616 B2
(45) Date of Patent: Oct. 15, 2024

(54) ENZYME-ENHANCED ADAMTS-13 ACTIVITY ASSAY

(71) Applicant: Siemens Healthcare Diagnostics Products GmbH, Marburg (DE)

(72) Inventors: Herbert Schwarz, Lohra (DE); Frank Vitzthum, Biedenkopf (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 0 days.

(21) Appl. No.: 18/317,511

(22) Filed: May 15, 2023

(65) Prior Publication Data
US 2023/0374564 A1    Nov. 23, 2023

(30) Foreign Application Priority Data
May 20, 2022  (EP) .................................... 22174472

(51) Int. Cl.
C12Q 1/37    (2006.01)
C12Q 1/32    (2006.01)

(52) U.S. Cl.
CPC ........ *C12Q 1/37* (2013.01); *C12Q 1/32* (2013.01)

(58) Field of Classification Search
CPC .................................. C12Q 1/37; C12Q 1/32
See application file for complete search history.

(56) References Cited

U.S. PATENT DOCUMENTS

| | | |
|---|---|---|
| 2005/0186646 A1 | 8/2005 | Cruz |
| 2007/0065895 A1 | 3/2007 | Miyata et al. |

FOREIGN PATENT DOCUMENTS

| | | | |
|---|---|---|---|
| EP | 1155328 A1 | 11/2001 | |
| WO | WO-2004005451 A3 | 4/2004 | |
| WO | WO-2009079618 A1 | 6/2009 | |
| WO | WO-2012071244 A1 * | 5/2012 | ............... C12Q 1/32 |
| WO | WO-2013071168 A1 | 5/2013 | |
| WO | WO-2013078216 A1 * | 5/2013 | ............... C12Q 1/32 |
| WO | WO-2022056313 A2 * | 3/2022 | ............... C12Q 1/37 |

OTHER PUBLICATIONS

Bartok et al., iGLuc: a luciferase-based inflammasome and protease activity reporter, Feb. 2013, Nat. Methods, 10(2): 147-154. (Year: 2013).*
Chiu et al., An Influenza Hemmaglutinin A Peptide Assay Based on the Enzyme-Multiplied Immunoassay Technique, 2011, Jour. of Immunoassay and Immunochemistry, 32:1, 1-17. (Year: 2011).*
Leach et al., Detection and Characterization of SUMO Protease Activity Using a Sensitive Enzyme-Based Reporter Assay, 2009, Methods in Molecular Biology: SUMO Protocols, vol. 497, Humana Press, 269-281. (Year: 2009).*

(Continued)

*Primary Examiner* — Yong D Pak
*Assistant Examiner* — Naghmeh Nina Moazzami
(74) *Attorney, Agent, or Firm* — Harness Dickey & Pierce P.L.C.

(57) ABSTRACT

A method and kit are provided herein for determining the ADAMTS-13 activity in a sample. The method comprises contacting the sample with a von Willebrand factor (VWF) polypeptide which has been coupled to a reporter enzyme, such as glucose-6-phosphate dehydrogenase (G6PDH).

13 Claims, 2 Drawing Sheets
Specification includes a Sequence Listing.

(56) References Cited

OTHER PUBLICATIONS

Zhang et al., Designing a Green Fluorogenic Protease Reporter by Flipping a Beta Strand of GFP for Imaging Apoptosis in Animals, 2019, Jour. of American Chemical Society, 141, 4526-4530. (Year: 2019).*

Kokame, K., et al., "FRETS-VWF73, a first fluorogenic substrate for ADAMTS13 assay," Bristish Journal of Haematology, 129: 93-100 (2005).

Kokame, K., et al., "VWF3, a region from D1596 t R1668 of von Willebrand factor, provides a minimal substrate for ADAMTS-13," Blood, 103(2): 607-612 (2004).

Wu, J.J., et al., "Characterization of a core binding site for ADAMTS13 in the A2 domain of von Willebrand factor," National Academy of Sciences of the USA, 103: 18470-18474 (2006).

Kostousov, V., et al., "Novel, semi-automated, 60-min-assay to determine von Willebrand factor cleaving activity of ADAMTS-13," Thrombosis Research, 118: 723-731 (2006).

Shelat, S.G., et al., "Molecular Biology of ADAMTS13 and Diagnostic Utility of ADAMTS13 Proteolytic Activity and Inhibitor Assays," Seminars in Thrombosis and Hemostatsis, 31(6):659-672 (2005).

* cited by examiner

SEQUENCE LISTING

Sequence total quantity: 25
SEQ ID NO: 1        moltype = AA  length = 73
FEATURE             Location/Qualifiers

```
                        source               1..73
                                             mol_type = protein
                                             organism = Homo sapiens
SEQUENCE: 1
DREQAPNLVY MVTGNPASDE IKRLPGDIQV VPIGVGPNAN VQELERIGWP NAPILIQDFE    60
TLPREAPDLV LQR                                                      73

SEQ ID NO: 2            moltype = AA  length = 73
FEATURE                 Location/Qualifiers
REGION                  1..73
                        note = Modified VWF73 Sequence
MOD_RES                 4
                        note = Dpr
MOD_RES                 15
                        note = Dpr
source                  1..73
                        mol_type = protein
                        organism = synthetic construct
SEQUENCE: 2
DREQAPNLVY MVTGNPASDE IKRLPGDIQV VPIGVGPNAN VQELERIGWP NAPILIQDFE    60
TLPREAPDLV LQR                                                      73

SEQ ID NO: 3            moltype = AA  length = 73
FEATURE                 Location/Qualifiers
REGION                  1..73
                        note = Mutant VWF73 (Q1599)
source                  1..73
                        mol_type = protein
                        organism = synthetic construct
SEQUENCE: 3
DREKAPNLVY MVTGNPASDE IKRLPGDIQV VPIGVGPNAN VQELERIGWP NAPILIQDFE    60
TLPREAPDLV LQR                                                      73

SEQ ID NO: 4            moltype = AA  length = 76
FEATURE                 Location/Qualifiers
source                  1..76
                        mol_type = protein
                        organism = Homo sapiens
SEQUENCE: 4
SQGDREQAPN LVYMVTGNPA SDEIKRLPGD IQVVPIGVGP NANVQELERI GWPNAPILIQ    60
DFETLPREAP DLVLQR                                                   76

SEQ ID NO: 5            moltype = AA  length = 76
FEATURE                 Location/Qualifiers
REGION                  1..76
                        note = Mutant VWF76 (Q1599)
source                  1..76
                        mol_type = protein
                        organism = synthetic construct
SEQUENCE: 5
SQGDREKAPN LVYMVTGNPA SDEIKRLPGD IQVVPIGVGP NANVQELERI GWPNAPILIQ    60
DFETLPREAP DLVLQR                                                   76

SEQ ID NO: 6            moltype = AA  length = 76
FEATURE                 Location/Qualifiers
REGION                  1..76
                        note = VWF76 (FRET)
MOD_RES                 7
                        note = Dpr
MOD_RES                 18
                        note = Dpr
source                  1..76
                        mol_type = protein
                        organism = synthetic construct
SEQUENCE: 6
SQGDREQAPN LVYMVTGNPA SDEIKRLPGD IQVVPIGVGP NANVQELERI GWPNAPILIQ    60
DFETLPREAP DLVLQR                                                   76

SEQ ID NO: 7            moltype = AA  length = 75
FEATURE                 Location/Qualifiers
source                  1..75
                        mol_type = protein
                        organism = Homo sapiens
SEQUENCE: 7
QGDREQAPNL VYMVTGNPAS DEIKRLPGDI QVVPIGVGPN ANVQELERIG WPNAPILIQD    60
FETLPREAPD LVLQR                                                    75

SEQ ID NO: 8            moltype = AA  length = 75
FEATURE                 Location/Qualifiers
```

```
REGION                    1..75
                          note = Mutant VWF75 (Q1599)
source                    1..75
                          mol_type = protein
                          organism = synthetic construct
SEQUENCE: 8
QGDREKAPNL VYMVTGNPAS DEIKRLPGDI QVVPIGVGPN ANVQELERIG WPNAPILIQD    60
FETLPREAPD LVLQR                                                    75

SEQ ID NO: 9              moltype = AA  length = 75
FEATURE                   Location/Qualifiers
REGION                    1..75
                          note = VWF75 (FRET)
MOD_RES                   6
                          note = Dpr
MOD_RES                   17
                          note = Dpr
source                    1..75
                          mol_type = protein
                          organism = synthetic construct
SEQUENCE: 9
QGDREQAPNL VYMVTGNPAS DEIKRLPGDI QVVPIGVGPN ANVQELERIG WPNAPILIQD    60
FETLPREAPD LVLQR                                                    75

SEQ ID NO: 10             moltype = AA  length = 74
FEATURE                   Location/Qualifiers
source                    1..74
                          mol_type = protein
                          organism = Homo sapiens
SEQUENCE: 10
GDREQAPNLV YMVTGNPASD EIKRLPGDIQ VVPIGVGPNA NVQELERIGW PNAPILIQDF    60
ETLPREAPDL VLQR                                                     74

SEQ ID NO: 11             moltype = AA  length = 74
FEATURE                   Location/Qualifiers
REGION                    1..74
                          note = Mutant VWF74 (Q1599)
source                    1..74
                          mol_type = protein
                          organism = synthetic construct
SEQUENCE: 11
GDREKAPNLV YMVTGNPASD EIKRLPGDIQ VVPIGVGPNA NVQELERIGW PNAPILIQDF    60
ETLPREAPDL VLQR                                                     74

SEQ ID NO: 12             moltype = AA  length = 74
FEATURE                   Location/Qualifiers
REGION                    1..74
                          note = VWF74 (FRET)
MOD_RES                   5
                          note = Dpr
MOD_RES                   16
                          note = Dpr
source                    1..74
                          mol_type = protein
                          organism = synthetic construct
SEQUENCE: 12
GDREQAPNLV YMVTGNPASD EIKRLPGDIQ VVPIGVGPNA NVQELERIGW PNAPILIQDF    60
ETLPREAPDL VLQR                                                     74

SEQ ID NO: 13             moltype = AA  length = 72
FEATURE                   Location/Qualifiers
source                    1..72
                          mol_type = protein
                          organism = Homo sapiens
SEQUENCE: 13
REQAPNLVYM VTGNPASDEI KRLPGDIQVV PIGVGPNANV QELERIGWPN APILIQDFET    60
LPREAPDLVL QR                                                       72

SEQ ID NO: 14             moltype = AA  length = 72
FEATURE                   Location/Qualifiers
REGION                    1..72
                          note = Mutant VWF72 (Q1599)
source                    1..72
                          mol_type = protein
                          organism = synthetic construct
SEQUENCE: 14
REKAPNLVYM VTGNPASDEI KRLPGDIQVV PIGVGPNANV QELERIGWPN APILIQDFET    60
LPREAPDLVL QR                                                       72
```

```
SEQ ID NO: 15            moltype = AA   length = 72
FEATURE                  Location/Qualifiers
REGION                   1..72
                         note = VWF72 (FRET)
MOD_RES                  3
                         note = Dpr
MOD_RES                  14
                         note = Dpr
source                   1..72
                         mol_type = protein
                         organism = synthetic construct
SEQUENCE: 15
REQAPNLVYM VTGNPASDEI KRLPGDIQVV PIGVGPNANV QELERIGWPN APILIQDFET   60
LPREAPDLVL QR                                                      72

SEQ ID NO: 16            moltype = AA   length = 71
FEATURE                  Location/Qualifiers
source                   1..71
                         mol_type = protein
                         organism = Homo sapiens
SEQUENCE: 16
EQAPNLVYMV TGNPASDEIK RLPGDIQVVP IGVGPNANVQ ELERIGWPNA PILIQDFETL   60
PREAPDLVLQ R                                                       71

SEQ ID NO: 17            moltype = AA   length = 71
FEATURE                  Location/Qualifiers
REGION                   1..71
                         note = Mutant VWF71 (Q1599)
source                   1..71
                         mol_type = protein
                         organism = synthetic construct
SEQUENCE: 17
EKAPNLVYMV TGNPASDEIK RLPGDIQVVP IGVGPNANVQ ELERIGWPNA PILIQDFETL   60
PREAPDLVLQ R                                                       71

SEQ ID NO: 18            moltype = AA   length = 71
FEATURE                  Location/Qualifiers
REGION                   1..71
                         note = VWF71(FRET)
MOD_RES                  2
                         note = Dpr
MOD_RES                  13
                         note = Dpr
source                   1..71
                         mol_type = protein
                         organism = synthetic construct
SEQUENCE: 18
EQAPNLVYMV TGNPASDEIK RLPGDIQVVP IGVGPNANVQ ELERIGWPNA PILIQDFETL   60
PREAPDLVLQ R                                                       71

SEQ ID NO: 19            moltype = AA   length = 70
FEATURE                  Location/Qualifiers
source                   1..70
                         mol_type = protein
                         organism = Homo sapiens
SEQUENCE: 19
QAPNLVYMVT GNPASDEIKR LPGDIQVVPI GVGPNANVQE LERIGWPNAP ILIQDFETLP   60
REAPDLVLQR                                                         70

SEQ ID NO: 20            moltype = AA   length = 70
FEATURE                  Location/Qualifiers
REGION                   1..70
                         note = Mutant VWF70 (Q1599, N1610 und K1617)
source                   1..70
                         mol_type = protein
                         organism = synthetic construct
SEQUENCE: 20
GAPNLVYMVT GCPASDEIRR LPGDIQVVPI GVGPNANVQE LERIGWPNAP ILIQDFETLP   60
REAPDLVLQR                                                         70

SEQ ID NO: 21            moltype = AA   length = 70
FEATURE                  Location/Qualifiers
REGION                   1..70
                         note = VWF70 (Fluorophore)
MOD_RES                  1
                         note = Dpr
MOD_RES                  12
                         note = Dpr
source                   1..70
```

```
                        mol_type = protein
                        organism = synthetic construct
SEQUENCE: 21
QAPNLVYMVT GNPASDEIKR LPGDIQVVPI GVGPNANVQE LERIGWPNAP ILIQDFETLP    60
REAPDLVLQR                                                           70

SEQ ID NO: 22           moltype = AA   length = 82
FEATURE                 Location/Qualifiers
source                  1..82
                        mol_type = protein
                        organism = Homo sapiens
SEQUENCE: 22
DHSFLVSQGD REQAPNLVYM VTGNPASDEI KRLPGDIQVV PIGVGPNANV QELERIGWPN    60
APILIQDFET LPREAPDLVL QR                                             82

SEQ ID NO: 23           moltype = AA   length = 115
FEATURE                 Location/Qualifiers
source                  1..115
                        mol_type = protein
                        organism = Homo sapiens
SEQUENCE: 23
EAQSKGDILQ RVREIRYQGG NRTNTGLALR YLSDHSFLVS QGDREQAPNL VYMVTGNPAS    60
DEIKRLPGDI QVVPIGVGPN ANVQELERIG WPNAPILIQD FETLPREAPD LVLQR        115

SEQ ID NO: 24           moltype = AA   length = 171
FEATURE                 Location/Qualifiers
source                  1..171
                        mol_type = protein
                        organism = Homo sapiens
SEQUENCE: 24
DVAFVLEGSD KIGEADFNRS KEFMEEVIQR MDVGQDSIHV TVLQYSYMVT VEYPFSEAQS    60
KGDILQRVRE IRYQGGNRTN TGLALRYLSD HSFLVSQGDR EQAPNLVYMV TGNPASDEIK   120
RLPGDIQVVP IGVGPNANVQ ELERIGWPNA PILIQDFETL PREAPDLVLQ R            171

SEQ ID NO: 25           moltype = AA   length = 2813
FEATURE                 Location/Qualifiers
source                  1..2813
                        mol_type = protein
                        organism = Homo sapiens
SEQUENCE: 25
MIPARFAGVL LALALILPGT LCAEGTRGRS STARCSLFGS DFVNTFDGSM YSFAGYCSYL    60
LAGGCQKRSF SIIGDFQNGK RVSLSVYLGE FFDIHLFVNG TVTQGDQRVS MPYASKGLYL   120
ETEAGYYKLS GEAYGFVARI DGSGNFQVLL SDRYFNKTCG LCGNFNIFAE DDFMTQEGTL   180
TSDPYDFANS WALSSGEQWC ERASPPSSSS NISSGEMQKG LWEQCQLLKS TSVFARCHPL   240
VDPEPFVALC EKTLCECAGG LECACPALLE YARTCAQEGM VLYGWTDHSA CSPVCPAGME   300
YRQCVSPCAR TCQSLHINEM CQERCVDGCS CPEGQLLDEG LCVESTECPC VHSGKRYPPG   360
TSLSRDCNTC ICRNSQWICS NEECPGECLV TGQSHFKSFD NRYFTFSGIC QYLLARDCQD   420
HSFSIVIETV QCADDRDAVC TRSVTVRLPG LHNSLVKLKH GAGVAMDGQD VQLPLLKGDL   480
RIQHTVTASV RLSYGEDLQM DWDGRGRLLV KLSPVYAGKT CGLCGNYNGN QGDDFLTPSG   540
LAEPRVEDFG NAWKLHGDCQ DLQKQHSDPC ALNPRMTRFS EEACVLTSP TFEACHRAVS   600
PLPYLRNCRY DVCSCSDGRE CLCGALASYA AACAGRGVR AWREPGRCEL NCPKGQVYLQ   660
CGTPCNLTCR SLSYPDEECN EACLEGCFCP PGLYMDERGD CVPKAQCPCY YDGEIFQPED   720
IFSDHHTMCY CEDGFMHCTM SGVPGSLLPD AVLSSPLSHR SKRSLSCRPP MVKLVCPADN   780
LRAEGLECTK TCQNYDLECM SMGCVSGCLC PPGMVRHENR CVALERCPCF HQGKEYAPGE   840
TVKIGCNTCV CQDRKWNCTD HVCDATCSTI GMAHYLTFDG LKYLFPGECQ YVLVQDYCGS   900
NPGTFRILVG NKGCSHPSVK CKKRVTILVE GGEIELFDGE VNVKRPMKDE THFEVVESGR   960
YIIILLLGKAL SVVWDRHLSI SVVLKQTYQE KVCGLCGNFD GIQNNDLTSS NLQVEEDPVD  1020
FGNSWKVSSQ CADTRKVPLD SSPATCHNNI MKQTMVDSSC RILTSDVFQD CNKLVDPEPY  1080
LDVCIYDTCS CESIGDCACF CDTIAAYAHV CAQHGKVVTW RTATLCPQSC EERNLRENGY  1140
ECEWRYNSCA PACQVTCQHP EPLACPVQCV EGCAHCPPG KILDELLQTC VDPEDCPVCE  1200
VAGRRFASGK KVTLNPSDPE HCQICHCDVV NLTCEACQEP GGLVVPPTDA PVSPTTLYVE  1260
DISEPPLHDF YCSRLLDLVF LLDGSSRLSE AEFEVLKAFV VDMMERLRIS QKWVRVAVVE  1320
YHDGSHAYIG LKDRKRPSEL RRIASQVKYA GSQVASTSEV LKYTLFQIFS KIDRPEASRI  1380
TLLLMASQEP QRMSRNFVRY VQGLKKKKVI VIPVGIGPHA NLKQIRLIEK QAPENKAFVL  1440
SSVDELEQQR DEIVSYLCDL APEAPPPTLP PDMAQVTVGP GLLGVSTLGP KRNSMVLDVA  1500
FVLEGSDKIG EADFNRSKEF MEEVIQRMDV GQDSIHVTVL QYSYMVTVEY PFSEAQSKGD  1560
ILQRVREIRY QGGNRTNTGL ALRYLSDHSF LVSQGDREQA PNLVYMVTGN PASDEIKRLP  1620
GDIQVVPIGV GPNANVQELE RIGWPNAPIL IQDFETLPRE APDLVLQRCS SGEGLQIPTL  1680
SPAPDCSQPL DVILLLDGSS SFPASYFDEM KSFAKAFISK ANIGPRLTQV SVLQYGSITT  1740
IDVPWNVVPE KAHLLSLVDV MQREGGPSQI GDALGFAVRY LTSEMHGARP GASKAVVILV  1800
TDVSVDSVDA AADAARSNRV TVFPIGIGDR YDAAQLRILA GPAGDSNVVK LQRIEDLPTM  1860
VTLGNSFLHK LCSGFVRICM DEDGNEKRPG DVWTLPDQCH TVTCQPDGQT LLKSHRVNCD  1920
RGLRPSCPNS QSPVKVEETC GCRWTCPCVC TGSSTRHIVT FDGQNFKLTG SCSYVLFQNK  1980
EQDLEVILHN GACSPGARQG CMKSIEVKHS ALSVELHSDM EVTVNGRLVS VPYVGGNMEV  2040
NVYGAIMHEV RFNHLGHIFT FTPQNNEFQL QLSPKTFASK TYGLCGICDE NGANDFMLRD  2100
GTVTTDWKTL VQEWTVQRPG QTCQPILEEQ CLVPDSSHCQ VLLLPLFAEC HKVLAPATFY  2160
AICQQDSCHQ EQVCEVIASY AHLCRTNGVC VDWRTPDFCA MSCPPSLVYN HCEHGCPRHC  2220
DGNVSSCGDH PSEGCFCPPD KVMLEGSCVP EEACTQCIGE DGVQHQFLEA WVPDHQPCQI  2280
CTCLSGRKVN CTTQPCPTAK APTCGLCEVA RLRQNADQCC PEYECVCDPV SCDLPPVPHC  2340
```

-continued

```
ERGLQPTLTN PGECRPNFTC ACRKEECKRV SPPSCPPHRL PTLRKTQCCD EYECACNCVN  2400
STVSCPLGYL ASTATNDCGC TTTTCLPDKV CVHRSTIYPV GQFWEEGCDV CTCTDMEDAV  2460
MGLRVAQCSQ KPCEDSCRSG FTYVLHEGEC CGRCLPSACE VVTGSPRGDS QSSWKSVGSQ  2520
WASPENPCLI NECVRVKEEV FIQQRNVSCP QLEVPVCPSG FQLSCKTSAC CPSCRCERME  2580
ACMLNGTVIG PGKTVMIDVC TTCRCMVQVG VISGFKLECR KTTCNPCPLG YKEENNTGEC  2640
CGRCLPTACT IQLRGGQIMT LKRDETLQDG CDTHFCKVNE RGEYFWEKRV TGCPPFDEHK  2700
CLAEGGKIMK IPGTCCDTCE EPECNDITAR LQYVKVGSCK SEVEVDIHYC QGKCASKAMY  2760
SIDINDVQDQ CSCCSPTRTE PMQVALHCTN GSVVYHEVLN AMECKCSPRK CSK         2813
```

ENZYME-ENHANCED ADAMTS-13 ACTIVITY ASSAY

CROSS-REFERENCE TO RELATED APPLICATION(S)

The present application claims priority under 35 U.S.C. § 119 to European Patent Application No. 22174472.5, filed 20 May 2022, the entire contents of which are incorporated herein by reference.

REFERENCE TO AN ELECTRONIC SEQUENCE LISTING

This application contains references to amino acid sequences and/or nucleic acid sequences which have been submitted concurrently herewith as the sequence listing xml file entitled "ST26_SL_12_May_2023", file size 36 Kilo-Bytes (KB), created on 12 May 2023. The aforementioned sequence listing is hereby incorporated by reference in its entirety.

FIELD

One or more example embodiments of the present invention relate to a method for determining the ADAMTS-13 activity in a sample, comprising contacting the sample with an inhibited reporter enzyme complex comprising a von Willebrand factor (VWF) polypeptide which has an ADAMTS-13 cleavage site and which has been coupled to a reporter enzyme. In another embodiment, the invention further relates to a kit comprising reagents which contain such an inhibited reporter enzyme complex, a reporter enzyme substrate and optionally one or more cofactors for the reporter enzyme. In another embodiment, the invention further relates to the use of such an inhibited reporter enzyme complex for determining the ADAMTS-13 activity in a biological sample.

BACKGROUND

ADAMTS-13 (A Disintegrin And Metalloproteinase with a Thrombospondin type 1 motif, member 13) is an enzyme which degrades von Willebrand factor (VWF) in vivo. There are congenital and acquired deficiencies of ADAMTS-13 enzyme activity that result in disorders, such as thrombotic thrombocytopenic purpura (TTP). A known assay for measuring the ADAMTS-13 activity in plasma samples works by determining the amount of degraded VWF activity by means of a ristocetin cofactor assay (WO 2004/005451 A2). This is achieved by adding VWF as substrate to a relatively small amount of sample, activating ADAMTS-13 and then degrading VWF over a very long incubation period (overnight). With this approach, it is critical that the sample itself contributes as little VWF as possible to the mix, since the activity thereof in plasma can be subject to high fluctuations. Furthermore, the substrate must not contribute any ADAMTS-13 activity to the mix, since it is only the ADAMTS-13 activity from the sample that is to be measured.

Analogously, a collagen binding assay can be used for detecting the loss of large VWF multimers (WO 0050904 A1). This ADAMTS-13 activity assay also has very long incubation periods, since only a small amount of plasma sample can be used and since native VWF is degraded very slowly.

The ADAMTS-13 activity assay was improved by using heat-treated VWF-deficient plasma. This reduced the incubation period to 60 minutes (see Kostousov et al., 2006, Thromb Res; 118(6):723-31). Another assay from the prior art uses VWF polypeptides as the substrate for ADAMTS-13. The cleavage products are quantitatively measured and correlated with the ADAMTS-13 activity (see US2007/065895 A1).

Another assay was described in US 2005/186646 A1. It uses polypeptides containing the cleavage site for ADAMTS-13 as the substrate. The formation of fragments is measured.

Another method was described by Kokame et al., 2005, Br. J. Haematol. 129:93-100. This approach uses a polypeptide substrate for determining the ADAMTS-13 activity, which substrate consists of 73 amino acid residues from the A2 domain of VWF, in particular from D1596 to R1668 of the A2 domain, and is referred to as VWF73. It was modified with FRET (fluorescence resonance energy transfer) reagents for detection. A similar approach is described in WO 2013/071168 A1, in which amino acid substitutions or deletions in the VWF polypeptide achieve more effective cleavage of the VWF polypeptide by ADAMTS-13. Cleavage is likewise detected by the FRET technique. However, classic coagulation analyzers normally do not provide the option of FRET detection technology, and so it is not possible to apply these approaches in such instruments.

Commercially available assays (e.g., Technozym ADAMTS-13 activity test or HemosIL Acustar ADAMTS-13 activity assay) use the VWF73 polypeptide as part of an antibody detection method. Here, the VWF73 polypeptide is immobilized on a solid phase which is contacted with the sample. The VWF fragments which are formed through the ADAMTS-13 activity are then recognized by antibodies. The disadvantage of these heterogeneous assays is the need for wash steps. They are therefore unsuitable for processing in routine coagulation analyzers.

SUMMARY

Therefore methods and means that make it possible to detect the ADAMTS-13 activity in a sample in an efficient, time-saving and automatable manner, are provided herein.

In an example embodiment, an object of the invention can be essentially achieved by mixing a sample with an inhibited reporter enzyme complex which comprises a von Willebrand factor (VWF) polypeptide having an ADAMTS-13 cleavage site and a reporter enzyme and which is activatable by the enzymatic cleavage of the VWF polypeptide by ADAMTS-13 and with a reporter enzyme substrate to form a reaction mixture and measuring the amount of reporter enzyme substrate in the reaction mixture that has been converted by the reporter enzyme activated by the ADAMTS-13 activity of the sample. The measured amount of converted reporter enzyme substrate is proportional to the ADAMTS-13 activity in the sample.

The effect of this is that the ADAMTS-13 activity in a sample can be determined in an efficient and time-saving manner and that the method can be carried out in a homogeneous assay format, i.e., without any wash steps, and is thus amenable to automated processing on common coagulation analyzers.

Thus, in one embodiment the present invention provides a method for determining the ADAMTS-13 activity in a sample, the method comprising the following steps:

a. providing a reaction mixture by mixing the sample with i. an inhibited reporter enzyme complex which comprises a von Willebrand factor (VWF) polypeptide having an ADAMTS-13 cleavage site and a reporter enzyme and which is activatable by the enzymatic cleavage of the VWF polypeptide by ADAMTS-13 and
   ii. a reporter enzyme substrate;
b. measuring the amount of reporter enzyme substrate in the reaction mixture that has been converted by the activated reporter enzyme,
   wherein the measured amount of converted reporter enzyme substrate is proportional to the ADAMTS-13 activity in the sample.

The reporter enzyme can be lysozyme, malate dehydrogenase, beta-galactosidase, alpha-amylase or glucose-6-phosphate dehydrogenase (G6PDH) or a functional variant thereof. A particularly preferred reporter enzyme is glucose-6-phosphate dehydrogenase (G6PDH). Optionally, one or more cofactors can be used or be present.

The measurement of the converted reporter enzyme substrate can be achieved by means of a spectrophotometric, luminometric (e.g., fluorescence determination) or electrochemical technique.

In a preferred embodiment, the VWF polypeptide having an ADAMTS-13 cleavage site and the reporter enzyme in the inhibited reporter enzyme complex are covalently linked to one another. Preference is given to linking via a spacer, most preferably via a spacer having 3 to 10 atoms.

It is further preferred that the VWF polypeptide comprises the A2 domain of VWF.

In particularly preferred embodiments of the invention, the VWF polypeptide has the amino acid sequence of any of SEQ ID NO: 1 to SEQ ID NO: 24.

The VWF polypeptide can be provided with an epitope tag at the C-terminus. Preferred epitope tags are biotin, FITC, streptavidin, GST, His, Flag, ACP, ELK16, HA or MBP.

In another embodiment of the method according to the invention, the inhibition of the reporter enzyme due to the coupling of the VWF polypeptide to the reporter enzyme is canceled by the ADAMTS-13 activity in the reaction mixture, this being achieved by proteolytic cleavage of the coupled VWF polypeptide by the ADAMTS-13 enzyme. Here, it is particularly preferred that the inhibition of the reporter enzyme caused by the coupled VWF polypeptide is enhanced by the binding of an antibody or some other specific binding partner, for example an aptamer or affimer, to the VWF polypeptide. Preferably, the inhibited reporter enzyme complex thus additionally comprises a binding partner from the group consisting of antibody, aptamer and affimer that has been specifically bound to the VWF polypeptide.

In a specific embodiment, the specifically bound binding partner in this case has been bound to an epitope tag on the VWF polypeptide.

The sample can be a body fluid, for example whole blood, blood plasma, blood serum, saliva, cerebrospinal fluid or lacrimal fluid.

In another embodiment, the present invention further provides a kit comprising a first reagent containing an inhibited reporter enzyme complex which comprises a VWF polypeptide having an ADAMTS-13 cleavage site and a reporter enzyme and which is activatable by the enzymatic cleavage of the VWF polypeptide by ADAMTS-13 and a second reagent containing a reporter enzyme substrate. Optionally, the kit comprises one or more cofactors for the reporter enzyme and/or for the ADAMTS-13 protease. The cofactor(s) can be present in the second reagent or in a separate third reagent.

In another embodiment, the present invention yet further provides for the use of an inhibited reporter enzyme complex which comprises a VWF polypeptide having an ADAMTS-13 cleavage site and a reporter enzyme and which is activatable by the enzymatic cleavage of the VWF polypeptide by ADAMTS-13 for determining the ADAMTS-13 activity in a sample.

DETAILED DESCRIPTION

Although the present invention is described with respect to particular embodiments, this description is not to be construed in a limiting sense.

Before describing in detail exemplary embodiments of the present invention, definitions important for understanding the present invention are given.

As used in this description and in the appended claims, the singular forms of "a" and "an" also include the respective plural forms, unless the context clearly dictates otherwise.

In connection with the present invention, the terms "approximately" and "about" refer to an interval of accuracy that a person skilled in the art understands to still ensure the technical effect of the feature in question. The term typically indicates a deviation from the indicated numerical value of ±20%, preferably ±15%, more preferably ±10% and even more preferably ±5%.

It is to be understood that the term "comprising" is not limiting. For the purposes of the present invention, the term "consisting of" or "essentially consisting of" is considered to be a preferred embodiment of the term "comprising of".

If hereinafter a group is defined to comprise at least a certain number of embodiments, this is meant to also encompass a group which preferably consists of these embodiments only.

Furthermore, the terms "(i)", "(ii)", "(iii)" or "(a)", "(b)", "(c)", "(d)" or "first", "second", "third", etc. and the like in the description or in the claims are used for distinguishing between similar elements and not necessarily for describing a sequential or chronological order.

It is to be understood that the terms so used are interchangeable under appropriate circumstances and that the embodiments of the invention described herein can be used in a different order than described herein. In case the terms relate to steps of a technique, method or use, there is no time or time interval coherence between the steps, i.e., the steps may be carried out simultaneously or there may be time intervals of seconds, minutes, hours, days, weeks, etc., between such steps, unless otherwise indicated.

It is to be understood that this invention is not limited to the particular methods, protocols, etc., described herein, since they may vary. It is also to be understood that the terminology used herein is for the purpose of describing particular embodiments only, and is not intended to limit the scope of the present invention that will be limited only by the appended claims.

The drawings are to be regarded as being schematic representations and elements illustrated in the drawings are not necessarily shown to scale. Rather, the various elements are represented such that their function and general purpose become apparent to a person skilled in the art. Unless defined otherwise, all technical and scientific terms used herein have the same meanings as commonly understood by a person of ordinary skill in the art.

As discussed above, in one embodiment the method according to the invention is suitable for homogeneous determination of the ADAMTS-13 activity in a biological sample. The term "homogeneous determination", as used herein, refers to the performance of the analysis in a homogeneous phase. This approach is rapid and uncomplicated, since there is no need to separate bound and unbound substances and no need for wash steps. Homogeneous determination involves "contacting" the sample with further reactants, preferably in a liquid phase, for example in a suitable buffer system.

Typically, the ADAMTS-13 activity is dependent on zinc and calcium ions. The presence thereof in the reaction mixture is preferred when carrying out an embodiment of the present method. Further optimal conditions are, for example, a pH of 6 (±1), a low ionic strength, 1-10 mM calcium ions and/or 0.01-1 mM zinc ions in the reaction mixture. In further embodiments, barium ions are present, especially when using citrate plasma, since this additionally stimulates the ADAMTS-13 activity via the release of citrate-bound calcium. In particular embodiments, pH 7.4 and 150 mM NaCl should be avoided, since the activity is reduced to ~75% under these conditions. In one embodiment, the method preferably envisages incubation at +37° C.

The "ADAMTS-13 activity", as described herein, refers to the "A Disintegrin And Metalloproteinase with a Thrombospondin type 1 motif, member 13" and is also referred to as "von Willebrand factor-cleaving protease" (VWFCP). ADAMTS-13 is a protease which is activated in the presence of zinc, calcium, barium and other metal ions. It is a plasma protein which cleaves von Willebrand factor (VWF) at the peptide bond between the amino acid residues Y1605 and M1606, thus limiting its size and hence also the adhesion for thrombocytes. In the event of reduced ADAMTS-13 activity, either through inherited mutations in the ADAMTS-13 gene or for example through the development of autoantibodies, the accumulation of very large VWF multimers can lead to thrombocyte aggregation and hence to microvascular thromboses. This corresponds to the potentially lethal syndrome of thrombotic thrombocytopenic purpura (TTP). Within the present invention, the activity of ADAMTS-13 is measured in the context of the cleavage of VWF.

"von Willebrand factor" or "VWF" is a large multimeric plasma glycoprotein of crucial importance for maintaining hemostasis, since it acts both as a carrier of antihemophilic factor and as a thrombocyte-vascular wall mediator in the blood coagulation system, especially by mediating the binding and adhesion of circulating thrombocytes at sites of vascular injury. Mutations in the VWF gene or deficits in this protein lead to von Willebrand disease (VWD). VWF is typically expressed by endothelial cells and megakaryocytes. What are synthesized are 250 kDa monomers, which are subjected to intracellular processing, glycosylation, multimerization and removal of propeptides, which ultimately leads to the formation of mature VWF multimers. The size of the VWF multimer is regulated by the ADAMTS-13 protease, which, as discussed above, cleaves the VWF protein at a particular singular site in the A2 domain of the VWF protein.

The VWF monomer is a protein of 2050 amino acids. The monomer contains a number of specific domains having particular functions. The monomer contains, inter alia, a D'/D3 domain, which binds to coagulation factor VIII; an A1 domain, which binds to the GPIb receptor of platelets, heparin and possibly collagen; an A2 domain, which must partially unfold in order to expose the unexposed cleavage site for ADAMTS-13; a A3 domain, which binds to collagen; a C4 domain, in which an RGD motif binds to the thrombocyte integrin αIIbβ3 when it has been activated; a "cystine knot" domain at the C-terminal end of the protein. After they have been expressed, the monomers are typically N-glycosylated and arranged to form dimers in the endoplasmic reticulum and to form multimers by crosslinking of cysteine residues via disulfide bonds in the Golgi apparatus.

The VWF polypeptide sequences encompassed by the present invention relate to the canonical human version of VWF isoform 1, which can be retrieved at https://www.uniprot.org with the accession number UniProtKB-P04275-1 (VWF_HUMAN). SEQ ID NO: 25 corresponds to the canonical human version of VWF isoform 1. The A2 domain, in which the ADAMTS-13 cleavage site is located, stretches from position 1498 to position 1668 of said canonical VWF isoform 1 (P04275-1). SEQ ID NO: 24 corresponds to the A2 domain of VWF and comprises positions D1498 to R1668.

The term "von Willebrand factor (VWF) polypeptide having an ADAMTS-13 cleavage site" used herein primarily refers to the A2 domain, which comprises the ADAMTS-13 cleavage site between Y1605 and M1606, or a fragment thereof, the fragment comprising the ADAMTS-13 cleavage site between Y1605 and M1606 (Tyr1605 and Met1606; based on the abovementioned canonical sequence). The fragment has a conformation allowing proteolytic cleavage by ADAMTS-13 at the cleavage site between Y1605 and M1606, i.e., it has a functional ADAMTS-13 cleavage site.

The VWF polypeptide can have different lengths and have one or more amino acid modifications compared to the abovementioned canonical sequence.

For instance, the VWF polypeptide can have, for example, a length of from 45 to 171 amino acids, for example from 65 to 171 amino acids, from 45 to 110 amino acids, from 45 to 76 amino acids, from 45 to 82 amino acids, from 50 to 73 amino acids or from 50 to 70 amino acids. More preferred are lengths of from 70 to 82 amino acids, from 72 to 110 amino acids or from 70 to 76 amino acids. In a further embodiment, the VWF polypeptide has a length of 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114 or 115 amino acids.

The VWF polypeptide having an ADAMTS-13 cleavage site can have one or more amino acid modifications. The modifications can be amino acid substitutions, deletions or additions, or chemical modifications of the amino acids. Said modifications can, in particular embodiments, have an influence on the cleavability and rate of cleavage by ADAMTS-13; they can alter the conformation of the polypeptide, influence the ways of folding the polypeptide or comprise a chemical modification, which are helpful for detection.

In preferred embodiments, the modifications concern positions 1599, 1610 and 1617 of SEQ ID NO: 25. More preferably, the amino acid at position 1599 of SEQ ID NO: 25 has been changed from Q to K and/or the amino acid at position 1610 of SEQ ID NO: 25 has been changed from N to C and/or the amino acid at position 1617 of SEQ ID NO: 25 has been changed from K to R.

In alternative embodiments, one or more amino acids can have been changed to 2,3-diaminopropionic acid (A2pr). Particularly preferably, the amino acid at position 1599 of SEQ ID NO: 25 has been changed from Q to 2,3-diaminopropionic acid (A2pr) and/or the amino acid at position 1610 of SEQ ID NO: 25 has been changed from N to 2,3-diaminopropionic acid (A2pr). In alternative embodiments, the amino acids changed to A2pr can be modified with a 2-(N-methylamino)benzoyl group and/or a 2,4-dinitrophenyl group. More preferably, the amino acid changed at position 1599 is modified with a 2-(N-methylamino)benzoyl group (Nma) and the amino acid changed at position 1610 is modified with a 2,4-dinitrophenyl group (Dnp). In this combination, the modified amino acids represent a FRET system in which excitation of the 2-(N-methylamino)benzoyl group by radiation of wavelength 340 nm is followed by transfer of fluorescence resonance energy to the so-called quencher, i.e., the 2,4-dinitrophenyl group.

Preferably, a VWF polypeptide comprises one of the sequences of SEQ ID NO: 1 to 24 of the sequence listing and as reproduced below in Table 1.

TABLE 1

| SEQ ID NO: | Sequence (N-term to C-term) | Comment |
|---|---|---|
| 1 | DREQAPNLVYMVTGNPASDEIKRLPGDIQVVPIGVGPNAN VQELERIGWPNAPILIQDFETLPREAPDLVLQR | VWF73 (D1596-R1668) |
| 2 | DRE - A2pr (*Nma*) - APNLVYMVTG - A2pr (*Dnp*) - PASDEIKRLPGDIQVVPIGVGPNANVQELER IGWPNAPILIQDFETLPREAPDLVLQR | VWF73 (FRET) |
| 3 | DREK̄APNLVYMVTGNPASDEIKRLPGDIQVVPIGVGPNAN VQEL̄ERIGWPNAPILIQDFETLPREAPDLVLQR | Mutated VWF73 (Q1599) |
| 4 | SQGDREQAPNLVYMVTGNPASDEIKRLPGDIQVVPIGVGP NANVQELERIGWPNAPILIQDFETLPREAPDLVLQR | VWF76 |
| 5 | SQGDREKAPNLVYMVTGNPASDEIKRLPGDIQVVPIGVGP NANVQEL̄ERIGWPNAPILIQDFETLPREAPDLVLQR | Mutated VWF76 (Q1599) |
| 6 | SQGDRE - A2pr (*Nma*) - APNLVYMVTG - A2pr (*Dnp*) - PASDEIKRLPGDIQVVPIGVGPNANVQELER IGWPNAPILIQDFETLPREAPDLVLQR | VWF76 (FRET) |
| 7 | QGDREQAPNLVYMVTGNPASDEIKRLPGDIQVVPIGVGPN ANVQELERIGWPNAPILIQDFETLPREAPDLVLQR | VWF75 |
| 8 | QGDREKAPNLVYMVTGNPASDEIKRLPGDIQVVPIGVGPN ANVQEL̄ERIGWPNAPILIQDFETLPREAPDLVLQR | Mutated VWF75 (Q1599) |
| 9 | QGDRE - A2pr (*Nma*) - APNLVYMVTG - A2pr (*Dnp*) - PASDEIKRLPGDIQVVPIGVGPNANVQELER IGWPNAPILIQDFETLPREAPDLVLQR | VWF75 (FRET) |
| 10 | GDREQAPNLVYMVTGNPASDEIKRLPGDIQVVPIGVGPNA NVQELERIGWPNAPILIQDFETLPREAPDLVLQR | VWF74 |
| 11 | GDREKAPNLVYMVTGNPASDEIKRLPGDIQVVPIGVGPNA NVQEL̄ERIGWPNAPILIQDFETLPREAPDLVLQR | Mutated VWF74 (Q1599) |
| 12 | GDRE - A2pr (*Nma*) - APNLVYMVTG - A2pr (*Dnp*) - PASDEIKRLPGDIQVVPIGVGPNANVQELER IGWPNAPILIQDFETLPREAPDLVLQR | VWF74 (FRET) |
| 13 | REQAPNLVYMVTGNPASDEIKRLPGDIQVVPIGVGPNANV QELERIGWPNAPILIQDFETLPREAPDLVLQR | VWF72 |

TABLE 1-continued

| SEQ ID NO: | Sequence (N-term to C-term) | Comment |
|---|---|---|
| 14 | REKAPNLVYMVTGNPASDEIKRLPGDIQVVPIGVGPNANV QE̲L̲ERIGWPNAPILIQDFETLPREAPDLVLQR | Mutated VWF72 (Q1599) |
| 15 | RE - A2pr (Nma) - APNLVYMVTG - A2pr (Dnp) - PASDEIKRLPGDIQVVPIGVGPNANVQELER IGWPNAPILIQDFETLPREAPDLVLQR | VWF72 (FRET) |
| 16 | EQAPNLVYMVTGNPASDEIKRLPGDIQVVPIGVGPNANVQ ELERIGWPNAPILIQDFETLPREAPDLVLQR | VWF71 |
| 17 | EKAPNLVYMVTGNPASDEIKRLPGDIQVVPIGVGPNANVQ EL̲ERIGWPNAPILIQDFETLPREAPDLVLQR | Mutated VWF71 (Q1599) |
| 18 | E - A2pr (Nma) - APNLVYMVTG - A2pr (Dnp) - PASDEIKRLPGDIQVVPIGVGPNANVQELER IGWPNAPILIQDFETLPREAPDLVLQR | VWF71 (FRET) |
| 19 | QAPNLVYMVTGNPASDEIKRLPGDIQVVPIGVGPNANVQE LERIGWPNAPILIQDFETLPREAPDLVLQR | VWF70 |
| 20 | GAPNLVYMVTGC̲PASDEIR̲RLPGDIQVVPIGVGPNANVQE L̲ERIGWPNAPIL̲IQDFETL̲PREAPDLVLQR | Mutated VWF70 (Q1599, N1610 and K1617) |
| 21 | A2pr (DyLIght 633) - APNLVYMVTG - A2pr (IRDye QC-1) - PASDEIR̲RLPGDIQVVPIGVGPNAN VQELERIGWPNAPILIQDFETL̲PREAPDLVLQR | VWF70 (Fluorophore) |
| 22 | DHSFLVSQGDREQAPNLVYMVTGNPASDEIKRLPGDIQVV PIGVGPNANVQELERIGWPNAPILIQDFETLPREAPDLVL QR | VWF82 (D1587-R1668) |
| 23 | EAQSKGDILQRVREIRYQGGNRTNTGLALRYLSDHSFLVS QGDREQAPNLVYMVTGNPASDEIKRLPGDIQVVPIGVGPN ANVQELERIGWPNAPILIQDFETLPREAPDLVLQR | VWF115 (E1554-R1668) |
| 24 | DVAFVLEGSDKIGEADFNRSKEFMEEVIQRMDVGQDSIHV TVLQYSYMVTVEYPFSEAQSKGDILQRVREIRYQGGNRTN TGLALRYLSDHSFLVSQGDREQAPNLVYMVTGNPASDEIK RLPGDIQVVPIGVGPNANVQELERIGWPNAPILIQDFETL PREAPDLVLQR | VWF-A2 (D1498-R1668) |

The term "inhibited reporter enzyme complex", as used herein, refers to a complex composed of a reporter enzyme and a VWF polypeptide having an ADAMTS-13 cleavage site, which complex serves for signal generation in the method according to the invention. The inhibited reporter enzyme complex is activatable by the enzymatic cleavage of the VWF polypeptide by ADAMTS-13, thus allowing the detection of ADAMTS-13 activity in a sample. The reporter enzyme activated as a consequence of the ADAMTS-13-mediated cleavage of the VWF polypeptide converts a reporter enzyme substrate depending on the presence or amount of ADAMTS-13 activity, and this is detectable. The measured amount of converted reporter enzyme substrate is proportional to the ADAMTS-13 activity in the sample. Detection can be achieved in different ways and with different methods. Preference is given here to spectrophotometric measurement, luminometric measurement, fluorescence determination and electrochemical detection. The nature and implementation of the detection depends on the reporter enzyme and on the reporter enzyme substrate used.

Detection methods can be calibrated with the aid of a control sample and/or a calibration sample. Reporter enzymes can be used in their native form, i.e., having a wild-type amino acid sequence, or they can have been genetically modified. For example, the amino acid sequence can be adapted to particular circumstances, for example the binding of reporter enzyme substrate can be optimized, or the expressability of the protein in particular host organisms can be influenced. Furthermore, covalent linkability with interactors can be achieved via the presence or introduction of additional amino acid residues such as cysteine, lysine, aspartic acid or glutamic acid.

In preferred embodiments, the reporter enzyme is a malate dehydrogenase, a beta-galactosidase, an alpha-amylase or a glucose-6-phosphate dehydrogenase.

Malate dehydrogenase (MDH) is an enzyme which dehydrogenates malate to form oxaloacetic acid while consuming $NAD^+$. The activity of MDH is typically determined by measuring the production of NADH in the MDH-catalyzed reaction Malate+$NAD^+$→Oxaloacetic Acid+NADH. Quantitative measurement of the reaction can, for example, be achieved spectrophotometrically by direct measurement at 340 nm, or be carried out colorimetrically after a downstream color reaction of the NADH with a dye, i.e., via the reduction of a reporter dye and the determination of the absorption at 450 nm. Alternatively, besides NAD+, it is also possible to use NADP+, thio-NAD+ or thio-NADP+.

beta-Galactosidase is an enzyme which hydrolyzes a beta-glycosidic bond between galactose and its organic binding partner. beta-Galactosidase is typically measured by using the colorless reporter substrate o-nitrophenyl-β-D-galactopyranoside (ONPG), which is converted into galactose and the chromophore o-nitrophenol, which can be quantified spectrophotometrically at 420 nm.

Glucose-6-phosphate dehydrogenase (G6PDH) is an enzyme which converts glucose-6-phosphate, using NAD+, into 6-phosphogluconolactone and NADH. Quantitative measurement of the reaction can, for example, be achieved spectrophotometrically by direct measurement of NADH at 340 nm, or be carried out colorimetrically after a downstream color reaction of the NADH with a dye, i.e., via the reduction of a reporter dye and the determination of the absorption at 450 nm. Alternatively, besides NAD+, it is also possible to use NADP+, thio-NAD+ or thio-NADP+. Further details can be found in suitable literature sources by a person skilled in the art.

Particular preference is given to the use of G6PDH as reporter enzyme.

The term "reporter enzyme substrate", as used herein, refers to a molecule which has an affinity for the active site of the reporter enzyme and can be converted thereby in a catalyzed reaction. The reporter enzyme substrate depends on the chosen reporter enzyme. Suitable reporter enzyme substrates for malate dehydrogenase (MDH) and glucose-6-phosphate dehydrogenase (G6PDH) are NAD+, NADP+, thio-NAD+ or thio-NADP+, which are converted into NADH, NADPH, thio-NADH or thio-NADPH. A suitable reporter enzyme substrate for beta-galactosidase is ONPG, which is converted, inter alia, into o-nitrophenol. Further reporter enzyme substrates in the context of particular reporter enzymes are known to a person skilled in the art.

In addition to the reporter enzyme substrate, one or more cofactors can additionally be used in the reaction mixture. In the context of the present invention, the term "cofactor" refers to a low-molecular-weight substance which contributes to the progress of a biochemical reaction. Cofactors can, for example, have been covalently or noncovalently bound to the reporter enzyme or incorporated therein. Examples of cofactors are ATP, ADP or metal ions, for example zinc, calcium, barium, magnesium or copper.

A suitable inhibited reporter enzyme complex which comprises a von Willebrand factor (VWF) polypeptide having an ADAMTS-13 cleavage site and a reporter enzyme and which is activatable by the enzymatic cleavage of the VWF polypeptide by ADAMTS-13 can be provided by coupling the VWF polypeptide to the reporter enzyme via a covalent bond. In the reporter enzyme, a covalent bond can, for example, be effected via the presence of a thiol or sulfhydryl group in a cysteine residue, the presence of an amino group in a lysine residue or the presence of a carboxyl group in an aspartic acid residue or glutamic acid residue. Typically, coupling is effected via activating molecules. For example, cysteines can react selectively with maleimides, disulfides, iodoacetamide, haloacetylene, aziridines, acryloyls, arylation agents, vinyl sulfones, pyridyl disulfides and other disulfides. Amino acids having side-chain primary amines, such as lysine, can be activated and linked by succinimide esters (N-hydroxysuccinimide, sulfosuccinimide or other succinimidyl esters) or particular isothiocyanates, such as PITC or FITC. Carboxyl groups can be coupled to amine groups by activation with carbodiimides. Further options are reductive alkylation and tosylation. Furthermore, it is possible to use photoreactive molecules, for example aryl azides or diazirines, as a reactive group of a covalent coupling to proteins. In this case, the reaction is triggered by UV irradiation. Covalent bonding is preferably carried out with an amino group at the N-terminus of the VWF polypeptide or with a carboxyl group at the C-terminus of the VWF polypeptide.

In further preferred embodiments, linkage is performed via a spacer. The term "spacer" refers to any structure of a molecular chain which covalently links the reporter enzyme to the VWF polypeptide. The spacer can consist of carbon atoms and nitrogen atoms and/or oxygen atoms and/or hydrogen atoms. For example, the molecular chain can have a total number of carbon atoms, nitrogen atoms and oxygen atoms, which are present in the main chain, of at least 3, preferably between 3 atoms and 100 atoms, more preferably between 3 atoms and 30 atoms, and even more preferably between 3 atoms and 20 atoms, for example 3, 4, 5, 6, 7, 8, 9, 10, 11, 12, 12, 14, 15, 16, 17, 18, 19, 20 atoms. Particular preference is given to a length of from 3 to 10 atoms. In another embodiment, the length of the main chain of the spacer can be from about 0.4 nm to about 100 nm and more preferably about between 0.6 nm and 30 nm, for example 0.6, 0.8, 1, 2, 4, 8, 10, 20, 25 or 30 nm. In further preferred embodiments, the spacer is a peptide spacer, for example a glycine spacer having between 2 and 10 glycine residues. In further embodiments, the spacer can be a hydrophilic spacer based on ethylene glycol.

The VWF polypeptide can be provided with a molecular epitope tag at the free terminus, i.e., at the terminus not coupled to the reporter enzyme. The molecular epitope tag can be attached at the N-terminus or at the C-terminus. Preference is given to attachment at the C-terminus of the VWF polypeptide. The term "molecular epitope tag", as used herein, refers to a small organochemical molecule or a short amino acid sequence which can be used as an epitope for antibody binding or as an interactor for molecular interactions with another binding partner. Examples of molecular epitope tags which can be used in the context of the invention are peptide tags such as the ALFA tag, Avi tag, C tag, calmodulin tag, polyglutamate tag, polyarginine tag, E tag, FLAG tag, HA tag, His tag, Gly-His tag, Myc tag, NE tag, Rho1D4 tag, S tag, SBP tag, Softag 1 tag, Softag 3 tag, Spot tag, Strep tag, T7 tag, TC tag, Ty tag, V5 tag, VSV tag, Xpress tag. Further examples include protein tags such as the BCCP tag, glutathione-S-transferase (GST) tag, the green fluorescent protein (GFP) tag, Halo tag, SNAP tag, CLIP tag, HUH tag, maltose binding protein tag, thioredoxin tag, Fc tag, CRDSAT tag or HiBiT tag. Particular preference is given to the tags biotin, FITC, streptavidin, GST, His, Flag, ACP, ELK16, HA or MBP. Alternatively, the epitope tag can be present in the form of a DNA oligonucleotide which hybridizes to a complementary DNA strand.

As illustrated in FIG. 1 and FIG. 2, an embodiment of the method according to the invention is based on the fact that inhibition of the reporter enzyme, which is caused by the coupling of the uncleaved VWF polypeptide, preferably a VWF polypeptide according to any of SEQ ID NO: 1 to SEQ ID NO: 24, and which contributes to the reporter enzyme being unable to interact or quantitatively interact with the reporter enzyme substrate, is canceled by the proteolytic ADAMTS-13 activity, i.e., by the ADAMTS-13-induced cleavage of the coupled VWF polypeptide at the cleavage site between Y1605 and M1606. As a result of the truncation of the coupled VWF polypeptide to a fragment which preferably ends with Y1605, or can also end with M1606, the blocking of the active site of the reporter enzyme is canceled. If the reactor enzyme substrate is present in the reaction mixture, the reporter enzyme can convert it quantitatively. The conversion of the substrate can be measured by measurement of the reaction products. Said measurement is a quantitative determination of the amount of ADAMTS-13 present in the sample used. The term "quantitative determination", as used herein, refers to the direct proportionality between the amount of ADAMTS-13 and the amount of reporter enzyme substrate converted by the reporter enzyme activated as a consequence of the proteolytic cleavage of the coupled VWF polypeptide. As a result, it is possible to represent the amount of ADAMTS-13 activity present in the reaction mixture.

Figure 1:
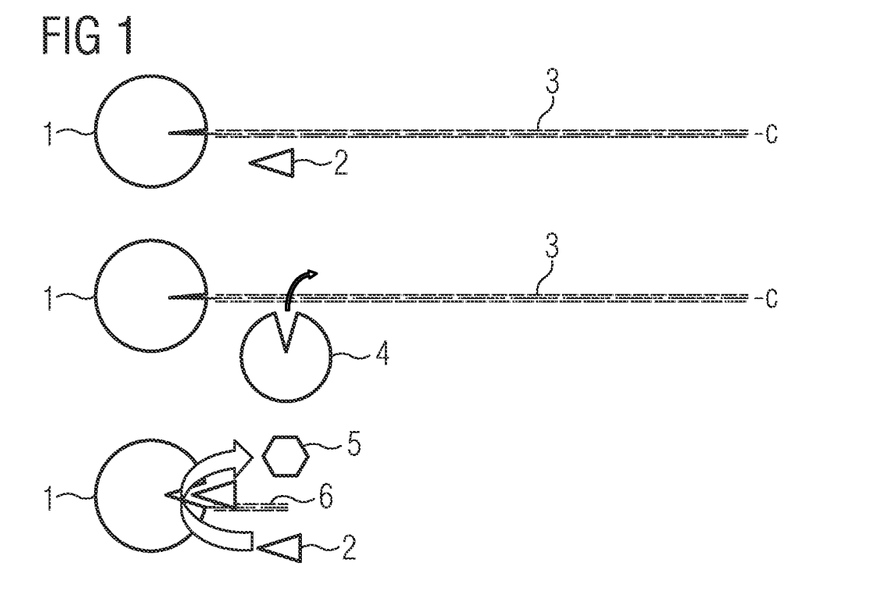
FIG. 1 shows one embodiment of the method according to the invention, in which a reporter enzyme (1) to which a VWF polypeptide (3) has been N-terminally coupled. The coupling of the VWF polypeptide (3) inhibits the activity of the reporter enzyme (1) and thereby prevents the conversion of a reporter enzyme substrate (2). Via proteolytic cleavage of the VWF polypeptide (3) by ADAMTS-13 (4), the VWF polypeptide (3) is cleaved, and what remains is just a fragment (6) on the reporter enzyme. This cancels or greatly reduces the inhibition of the reporter enzyme (1), and so the reporter enzyme substrate (2) can now interact with the reporter enzyme (1) and is converted into a detectable product (5).
Figure 2:
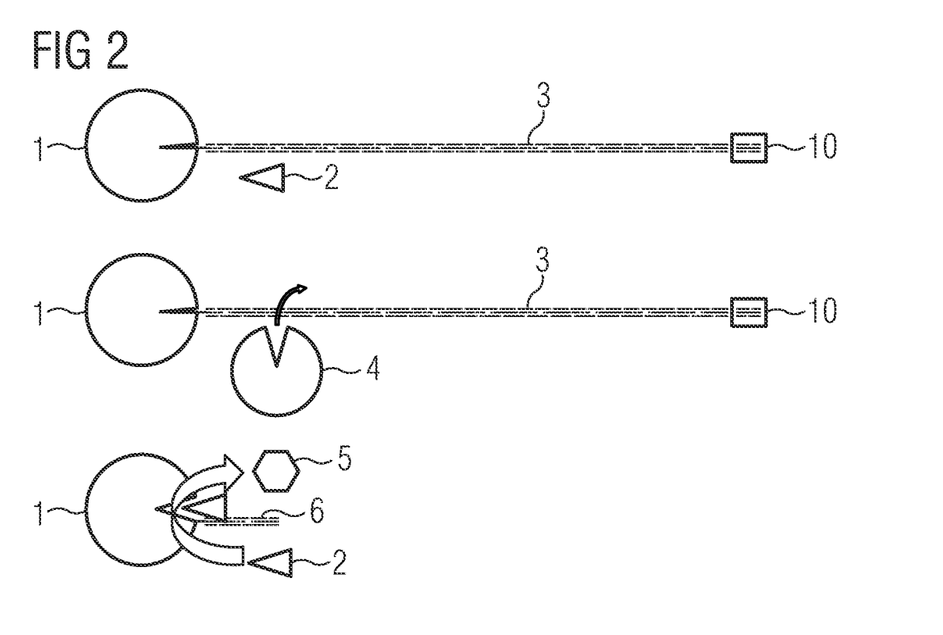
FIG. 2 shows a further embodiment of the method according to the invention that substantially corresponds to the method shown in FIG. 1, with the difference that the VWF polypeptide (3) is C-terminally linked to an epitope tag (10). Said epitope tag can be used for regulation of the inhibition of the reporter enzyme (1) or for removal purposes after a proteolytic step.
Figure 3:
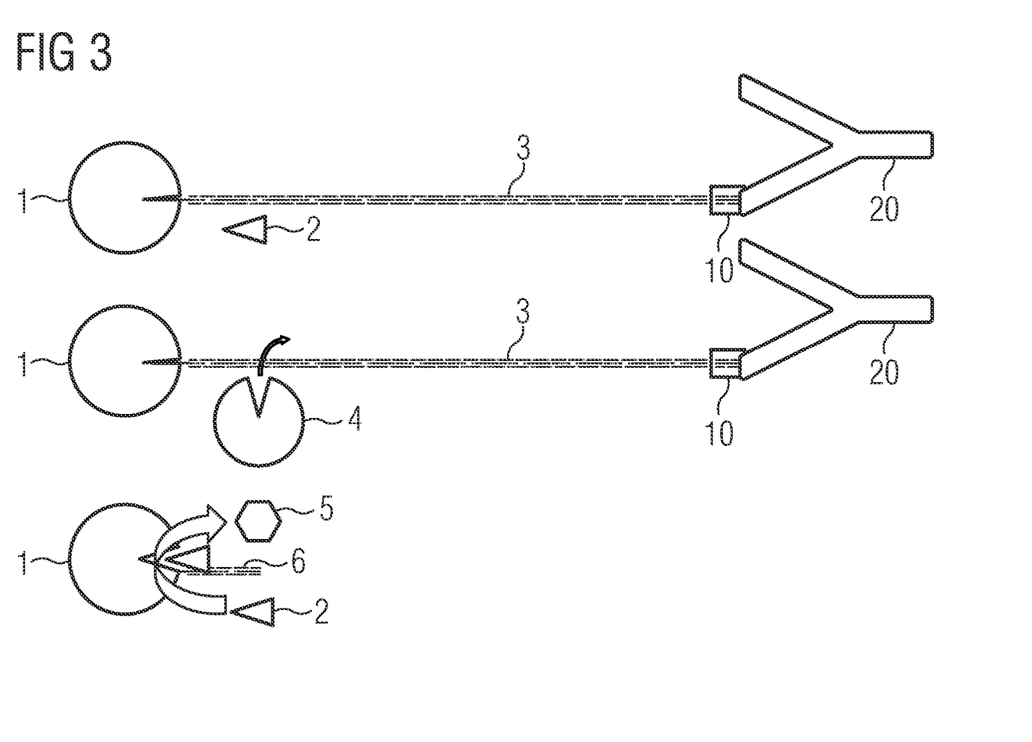
FIG. 3 shows a further embodiment of the method according to the invention that substantially corresponds to the method shown in FIG. 2, with the difference that an antibody or some other specific binding partner (20) has been bound to the C-terminal epitope tag (10) of the VWF polypeptide (3). This interaction can be used for regulation of the inhibition of the reporter enzyme (1) or for removal purposes after a proteolytic step.

In a further embodiment which is illustrated in FIG. 3 for example, the inhibition due to the coupled VWF polypeptide is enhanced by the binding of a binding partner to the distal end of the VWF polypeptide. The "distal" end of the coupled VWF polypeptide is to be understood to mean the end of the polypeptide that is opposite to the site of coupling with the reporter enzyme, or a more remote region of the polypeptide as viewed from the site of coupling. Said end is preferably the uncoupled C-terminus of the polypeptide, but can alternatively also be the uncoupled N-terminus. The term "binding partner", as used herein, refers to all units known to a person skilled in the art that can specifically bind said distal region of the polypeptide. In further specific embodiments, the binding site of the binding partners can be at other sites or in other regions of the coupled VWF polypeptide, for example it can be an epitope in the nondistal region. Preferably, such a binding site is distal to the ADAMTS-13 cleavage site between Y1605 and M1606 in the VWF polypeptide. More preferably, a molecular epitope tag, for example as defined above, which can preferably be recognized by an antibody or some other binding partner is present at the distal end. In further preferred embodiments, a terminal epitope which can be recognized by an antibody is present.

The additional binding of a binding partner to the VWF polypeptide, preferably to a region of the VWF polypeptide that is cleaved off from the reporter enzyme complex in the presence of ADAMTS-13, enhances the inhibition of the reporter enzyme during the absence of proteolytic cleavage of the VWF polypeptide.

A binding partner for enhancing the inhibition of the reporter enzyme complex includes, for example, specifically binding antibodies, aptamers or affimers. Additionally included are artificial antibody mimetics, i.e., polymeric organic or inorganic structures which specifically bind a target molecule, typically with a binding affinity within the range of an antibody.

The term "antibody", as used herein, refers to immunoglobulin molecules and immunologically active parts of immunoglobulin molecules, i.e., molecules which contain an antigen-binding site which immunospecifically binds an antigen. The immunoglobulin molecules of the invention can be of any type (e.g., IgG, IgE, IgM, IgD, IgA and IgY) and any class (e.g., IgG1, IgG2, IgG3, IgG4, IgA1 and IgA2) or subclass of immunoglobulin molecules. In further embodiments, antibodies of the invention include polyclonal, monoclonal, multispecific, murine, human, humanized or chimeric antibodies, or entire immunoglobulin molecules.

The term "aptamer", as used herein, refers to a peptide or a nucleic acid which specifically binds to a target epitope. Aptamers are typically selected from pools of nucleic acids and/or peptides on the basis of their selective binding properties. A "nucleic acid aptamer" is a short nucleic acid molecule, for example RNA, DNA, PNA, CNA, HNA, LNA or ANA, or any other suitable nucleic acid format known to a person skilled in the art, which is capable of specifically binding to a protein target molecule. A "peptide aptamer" is a short peptide which is capable of interacting with a protein target and being specifically bound thereto. Typically, peptide aptamers comprise a variable peptide loop which is bound at both ends to a protein scaffold. It is assumed that this twin structural constraint greatly increases the binding affinity of the peptide aptamer, so that it is comparable with that of an antibody. The variable loop length can preferably be composed of ten to twenty amino acids.

A preferred subform of the peptide aptamer is the "affimer". This is an artificially generated protein from the group of the cystatins. Affimers are based on the protease inhibitor cystatin A and are individually modified at the molecule surface by protein design. As a result, a specific affimer can bind to specifically chosen molecules. The cystatin component serves as the scaffold for stabilization of the conformation of a, for example, sequence inserted in the surface, for instance an alpha-helix. Advantageously, affimers have a high biological half-life and thermostability and can be used stably over a relatively long period.

The presence of a binding partner which is specifically bound at the distal end of the VWF polypeptide increases the inhibitory effect of the coupled VWF polypeptide. In specific embodiments, it is thereby possible to use relatively short VWF fragments, as described above, having amino acid lengths of between 45 and 171 amino acids that comprise a functional ADAMTS-13 cleavage site.

The term "sample", as used herein, includes vertebrate body fluids, preferably mammalian body fluids, more preferably human body fluids. Included are all types of body fluids in which ADAMTS-13 activity may be present. Preference is given to, in particular, whole blood, blood plasma, blood serum, saliva, cerebrospinal fluid or lacrimal fluid.

Another embodiment of the invention relates to a kit comprising a first reagent containing an inhibited reporter enzyme complex which comprises a von Willebrand factor (VWF) polypeptide having an ADAMTS-13 cleavage site and a reporter enzyme, which is activatable by the enzymatic cleavage of the VWF polypeptide by ADAMTS-13, and a second reagent containing a reporter enzyme substrate and optionally one or more cofactors for the reporter enzyme, as described herein. The kit can furthermore, in particular embodiments, contain binding partners such as antibodies, aptamers or affimers. The reporter enzyme and the VWF polypeptide correspond to the definitions and descriptions provided herein in the context of the method, or as explained in the illustrative, nonlimiting figures.

The kit in one embodiment according to the invention is a diagnostic composition for the in vitro determination of the ADAMTS-13 activity in a sample of an individual, for example a patient or a person, in order for example to be able to determine a deficiency of ADAMTS-13 activity or the level of ADAMTS-13 activity. As a result, it is additionally possible to determine the presence of thrombotic thrombocytopenic purpura (TTP) or the predisposition for TTP. In addition, the kit can contain a package insert with instructions for use. Furthermore, the kit can contain one or more positive controls and/or one or more calibrators having defined ADAMTS-13 activity. A kit in another embodiment according to the invention can further contain a sample diluent and/or a substrate buffer.

Another embodiment of the present invention relates to the use of an inhibited reporter enzyme complex which comprises a VWF polypeptide having an ADAMTS-13 cleavage site and a reporter enzyme and which is activatable by the enzymatic cleavage of the VWF polypeptide by ADAMTS-13 for determining ADAMTS-13 activity in a biological sample. The reporter enzyme and the VWF polypeptide correspond to the definitions and descriptions provided herein in the context of the method, or as explained in the illustrative, nonlimiting figures. The use is likewise based on the use of binding partners such as antibodies, aptamers or affimers as defined above or illustrated in the nonlimiting figures.

The following examples and figures are provided for illustrative purposes. It is thus to be understood that the examples and figures are not to be construed as limiting. A person skilled in the art will clearly be able to envisage further modifications of the principles laid out herein.

EXAMPLES

Example 1

A) VWF73-G6PDH Conjugation for Producing an Inhibited G6PDH-VWF Reporter Enzyme Complex Using an NHS ester-activated VWF73 polypeptide (SEQ ID NO: 1), covalent coupling was carried out to G6PDH (glucose-6-phosphate dehydrogenase from L. mesenteroides; lyophilized powder in 100 mM sodium phosphate buffer (SPB), pH 7.3) via NH2 groups of the G6PDH. Here, 100 U/mL G6PDH were coupled with 1 mM VWF73 polypeptide at room temperature for 4 hours. Excess VWF73 polypeptide was then removed via gel filtration using PD-10 columns (Amersham Biosciences) and/or centrifugal filtration using, for example, Microcon YM-30 (Millipore). All the steps were performed at room temperature.

B) Determination of ADAMTS-13 Activity in Accordance with the Invention

One embodiment of the method according to the invention was processed in an automated manner on an Atellica COAG 360 System (Siemens Healthineers). This comprised mixing of 30 μL of VWF73-G6PDH conjugate (0.5 U/mL) (reagent 1) with 30 μL of sample and with 50 μL of activation buffer (reagent 2=20 mM BIS-TRIS, pH 6.0, 12.5 mM BaCl2, 5 mM ZnCl2, 1.5 mM CaCl2 and 0.05% Tween-20) and incubation at +37° C. for 20 min. Thereafter, 130 μL of substrate solution (reagent 3=0.018 M glucose-6-phosphate and 0.018 M NAD+ in 55 mM Tris-HCl buffer with 3.3 mM MgCl2, pH 7.8) preadjusted to a temperature of +37° C. were added to the reaction mixture, and the increase in the absorption of the reaction mixture in mOD (as a consequence of the formation of NADH+H+ as a result of reduction of NAD+ via the G6PDH activity) was measured at 340 nm for two minutes. The mOD measurement values were used to determine the reaction rate of the enzymatic reaction (delta mOD/min, Δm OD/min).

In this way, citrate plasma samples of five healthy donors, of two donors with thrombotic thrombocytopenic purpura (TTP) and of one donor with autoantibodies against ADAMTS-13, but without clinical diagnosis of TTP, were tested in three independent reactions in each case, and the average was calculated (see Table 3).

The ADAMTS-13 activity in a sample was determined by making a comparison with an ADAMTS-13 standard curve prepared from a dilution series of FFP (fresh frozen plasma pool) from >80 citrate plasmas of healthy donors (normal plasma) having 100% arbitrary ADAMTS-13 activity diluted with ADAMTS-13-deficient plasma (0%-100% ADAMTS-13 activity). Each dilution step was tested in three independent reactions in each case, and the average was calculated (see Table 2).

TABLE 2

| Proportion of normal plasma in ADAMTS-13-deficient plasma; ADAMTS-13 activity (% of the norm) | Δ mOD/min Measurement 1 | Δ mOD/min Measurement 2 | Δ mOD/min Measurement 3 | Δ mOD/min Average |
|---|---|---|---|---|
| 0% | 207.9 | 207.8 | 207.3 | 207.7 |
| 5% | 215.6 | 216.5 | 213.9 | 215.3 |
| 10% | 221.1 | 221.3 | 218.8 | 220.4 |
| 25% | 232.2 | 232.7 | 232.6 | 232.5 |
| 50% | 255.3 | 257.3 | 254.0 | 255.5 |
| 75% | 285.9 | 287.6 | 285.9 | 286.5 |
| 100% | 310.2 | 312.1 | 310.9 | 311.1 |

The results in Table 2 show that the cleavage of the VWF73 polypeptide of the VWF73-G6PDH conjugate and the associated reactivation of the G6PDH activity occurs in a concentration-dependent manner with respect to ADAMTS-13 activity. As ADAMTS-13 activity increases (in % of the norm), the cleavage rate of the coupled VWF73 polypeptide increases, and the associated reactivation of the G6PDH activity leads to the increase in the absorption of the reaction at a wavelength of 340 nm. The results of the experiment also show that, by means of the described method, an ADAMTS-13 activity of 5% of the norm can still be sufficiently distinguished from a sample without ADAMTS-13 activity (ADAMTS-13-deficient plasma).

TABLE 3

| Patient plasma | Δ mOD/min Measurement 1 | Δ mOD/min Measurement 2 | Δ mOD/min Measurement 3 | Δ mOD/min Average |
|---|---|---|---|---|
| Healthy donor 01 | 308.9 | 309.5 | 310.9 | 309.8 |
| Healthy donor 02 | 310.1 | 310.9 | 312.3 | 311.1 |
| Healthy donor 03 | 305.1 | 308.7 | 306.1 | 306.6 |
| Healthy donor 04 | 311.9 | 310.9 | 308.8 | 310.5 |
| Healthy donor 05 | 315.1 | 312.3 | 314.1 | 313.8 |
| TTP patient 01 | 217.6 | 219.1 | 218.2 | 218.3 |
| TTP patient 02 | 220.1 | 215.4 | 213.9 | 216.5 |
| Patient with ADAMTS-13 autoantibodies | 227.3 | 228.4 | 228.9 | 228.2 |

Table 3 shows that, by means of the described method, TTP patient samples (TTP patient 01 with 9% of the norm and TTP patient 02 with 7% of the norm) or patient samples with ADAMTS-13 autoantibodies (patient with 21% of the norm) having decreased ADAMTS-13 activity can be clearly differentiated from samples of healthy blood donors. A strong reduction in the ADAMTS-13 activity in blood (<5-10% residual activity) is considered to be a specific indication of classic TTP (thrombotic thrombocytopenic purpura) (congenital or acquired).

What is claimed is:

1. A method for determining ADAMTS-13 activity in a sample, the method comprising:
    mixing the sample with
        an inhibited reporter enzyme complex which comprises a von Willebrand factor (VWF) polypeptide having an ADAMTS-13 cleavage site and a reporter enzyme and which is activatable by the enzymatic cleavage of the VWF polypeptide by ADAMTS-13, and
        a reporter enzyme substrate to produce a reaction mixture; and
    measuring the amount of reporter enzyme substrate in the reaction mixture that has been converted by the activated reporter enzyme;
    wherein the measured amount of converted reporter enzyme substrate is proportional to the ADAMTS-13 activity in the sample; and
    wherein the reporter enzyme is glucose-6-phosphate dehydrogenase (G6PDH) from L, mesentroides or a functional variant thereof.

2. The method as claimed in claim 1, wherein the measurement of the converted reporter enzyme substrate is achieved by means of a spectrophotometric, luminometric or electrochemical technique.

3. The method as claimed in claim 1, wherein the inhibited reporter enzyme complex comprises a VWF polypeptide having an ADAMTS-13 cleavage site covalently linked to the reporter enzyme.

4. The method as claimed in claim 3, wherein the VWF polypeptide having the ADAMTS-13 cleavage site and the reporter enzyme are covalently linked to one another via a spacer.

5. The method as claimed in claim 4, wherein the spacer has 3 to 10 atoms.

6. The method as claimed in claim 1, wherein the VWF polypeptide comprises the A2 domain of VWF.

7. The method as claimed in claim 1, wherein the VWF polypeptide comprises the amino acid sequence of any of SEQ ID NO: 1 to SEQ ID NO: 24.

8. The method as claimed in claim 1, wherein the VWF polypeptide has an epitope tag at the C-terminus.

9. The method as claimed in claim 8, wherein the epitope tag is biotin, FITC, streptavidin, GST, His, Flag, ACP, ELK16, HA or MBP.

10. The method as claimed in claim 1, wherein the inhibited reporter enzyme complex additionally comprises a binding partner selected from the group consisting of antibody, aptamer and affimer that has been specifically bound to the VWF polypeptide.

11. The method as claimed in claim 10, wherein the specifically bound binding partner has been bound to an epitope tag on the VWF polypeptide.

12. The method as claimed in claim 1, wherein the sample is a body fluid.

13. The method as claimed in claim 12, wherein the body fluid is whole blood, blood plasma, blood serum, saliva, cerebrospinal fluid or lacrimal fluid.

* * * * *